United States Patent
Pedrazzini

(10) Patent No.: US 9,868,593 B2
(45) Date of Patent: Jan. 16, 2018

(54) MULTIPLE RACK APPARATUS FOR ACCOMMODATING BIOLOGICAL PRODUCT CONTAINERS UNLOADED FROM A STORAGE FOR THE PRESERVATION OF THE SAME INTERFACED WITH A LABORATORY AUTOMATION SYSTEM

(71) Applicant: Inpeco Holding Ltd., Qormi (MT)

(72) Inventor: Gianandrea Pedrazzini, Paradiso (CH)

(73) Assignee: INPECO HOLDING LTD., Qormi (MT)

( * ) Notice: Subject to any disclaimer, the term of this patent is extended or adjusted under 35 U.S.C. 154(b) by 0 days.

(21) Appl. No.: 14/406,373

(22) PCT Filed: Jun. 20, 2013

(86) PCT No.: PCT/EP2013/062833
§ 371 (c)(1),
(2) Date: Dec. 8, 2014

(87) PCT Pub. No.: WO2014/001184
PCT Pub. Date: Jan. 3, 2014

(65) Prior Publication Data
US 2015/0183586 A1 Jul. 2, 2015

(30) Foreign Application Priority Data
Jun. 25, 2012 (IT) ................ MI2012A1111

(51) Int. Cl.
*B65G 65/32* (2006.01)
*B65G 43/00* (2006.01)
(Continued)

(52) U.S. Cl.
CPC .......... *B65G 35/06* (2013.01); *A01N 1/0252* (2013.01); *B65G 43/00* (2013.01); *B65G 65/32* (2013.01);
(Continued)

(58) Field of Classification Search
CPC .. B65G 65/32; B65G 2203/042; B65B 67/02; G01N 35/02–35/04
(Continued)

(56) References Cited

U.S. PATENT DOCUMENTS 3,650,085 A * 3/1972 Bay .................. G07D 9/065
53/254
3,828,833 A * 8/1974 Smith ................ B65B 31/025
141/181
(Continued)

FOREIGN PATENT DOCUMENTS

DE 202007002753 U1 4/2007
EP 2148208 A2 1/2010

*Primary Examiner* — Anna Momper
*Assistant Examiner* — Ashley Romano
(74) *Attorney, Agent, or Firm* — Jacobson Holman, PLLC.

(57) ABSTRACT

There is described a multiple rack apparatus for accommodating biological product containers unloaded from a storage for the preservation of the same interfaced with a laboratory automation system, comprising an odd number of said racks which can be housed within a platform having a number of locations, which is equal to said odd number plus one. Said racks can horizontally or vertically slide from one location to another of said platform, taking advantage of the presence of a temporarily empty location, said racks further occupying in turn an operating location which, being vertical with respect to an outlet tube of said storage, accommodates said biological product containers unloaded from said storage.

8 Claims, 4 Drawing Sheets

(51) Int. Cl.
    *A01N 1/02*     (2006.01)
    *B65G 35/06*     (2006.01)
    *G01N 35/04*     (2006.01)
    *G01N 35/00*     (2006.01)

(52) U.S. Cl.
    CPC ....... *G01N 35/00603* (2013.01); *G01N 35/04* (2013.01); *B65G 2203/0283* (2013.01); *B65G 2203/042* (2013.01)

(58) Field of Classification Search
    USPC .................................................. 414/331.03
    See application file for complete search history.

(56) References Cited

U.S. PATENT DOCUMENTS

| | | | | |
|---|---|---|---|---|
| 5,039,273 | A * | 8/1991 | Schuhmacher | B65G 65/32 414/301 |
| 5,369,940 | A * | 12/1994 | Soloman | B65B 57/20 53/500 |
| 6,068,437 | A * | 5/2000 | Boje | B65G 1/127 198/346.2 |
| 6,422,802 | B1 * | 7/2002 | Herrin | B65B 19/12 414/419 |
| 7,214,023 | B2 * | 5/2007 | Sato | B65G 1/0435 414/281 |
| 2002/0046551 | A1 * | 4/2002 | Tisma | B65B 43/60 53/506 |
| 2007/0172396 | A1 * | 7/2007 | Neeper | G01N 35/00732 422/400 |
| 2010/0028124 | A1 * | 2/2010 | Lackner | G01N 35/0099 414/806 |
| 2010/0303590 | A1 | 12/2010 | Pedrazzini | |
| 2010/0316473 | A1 * | 12/2010 | Cartal | B07C 1/025 414/404 |

\* cited by examiner

MULTIPLE RACK APPARATUS FOR ACCOMMODATING BIOLOGICAL PRODUCT CONTAINERS UNLOADED FROM A STORAGE FOR THE PRESERVATION OF THE SAME INTERFACED WITH A LABORATORY AUTOMATION SYSTEM

The present invention relates to a multiple rack apparatus for accommodating biological product containers unloaded from a storage for the preservation of the same interfaced with a laboratory automation system.

Nowadays, the presence of storages for preserving biological material samples at advantageously very low, controlled temperatures is increasingly frequent along automated systems in the biological material sample test laboratories. The purpose is to ensure the integrity of such samples and the possibility of reusing the samples which were previously processed by the various modules along the automation system even several days after the collection. Very often, carrying out a second series of tests on the same sample is required in order to check, and possibly validate, the obtained results, and it is therefore advantageous to preserve the sample appropriately.

Reference should be made to patent EP-2240787 previously filed by the Applicant for a more detailed description of a storage of this type.

After having established that the sample is no longer needed and may therefore be eliminated, or that its lifespan has more simply expired (and therefore testing is no longer possible because the sample is no longer intact), it must be eliminated from the storage, and this is obtained by routing the biological material container, or test tube, towards an appropriate outlet tube, from where the sample is ejected.

A single unloading collector used for accommodating the ejected test tubes is positioned by the side of the storage in the known solutions.

Problems occur in a solution of this type because the presence of a single unloading collector presumes that, once filled, it must be emptied and naturally during this operation the activity of the storage must be stopped in order to prevent the ejection of test tubes through the outlet tube precisely while the unloading collector is not present because the operator is unloading it.

As a consequence of this, and considering the increasingly high operating volumes of a test laboratory and the fact that test tubes may thus be unloaded from the store constantly during the day, a considerably more spacious device for collecting the ejected test tubes would be advantageous, without this being a larger sized unloading collector. Possibly, the high capacity of the above apparatus must ensure that it may be kept working during the night, and thus be combined with keeping the storage operating during the night.

These and other objects are achieved by a multiple rack apparatus for accommodating biological product containers unloaded from a storage for the preservation of the same interfaced with a laboratory automation system, characterized in that it comprises an odd number of said racks which can be housed within a platform having a number of locations which is equal to said odd number plus one, said racks horizontally or vertically sliding from one location to another of said platform, taking advantage of the presence of a temporarily empty location, said racks further occupying in turn an operating location which, being vertical with respect to an outlet tube of said storage, accommodates said biological product containers unloaded from said storage.

These and other features of the present invention will become further apparent from the following detailed description of an embodiment thereof, shown by way of non-limitative example in the accompanying drawings, in which.

Figure 1:
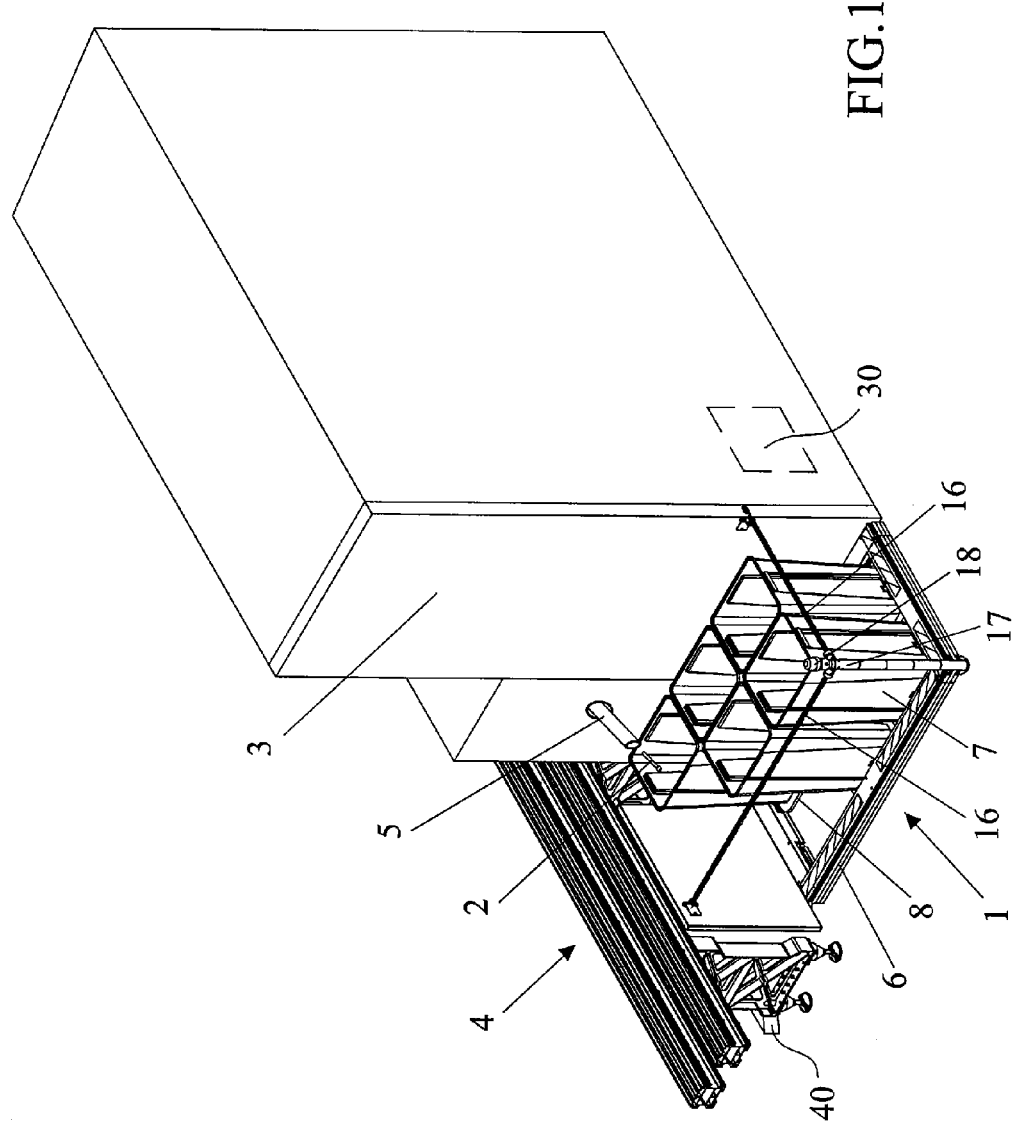
FIG. 1 shows a perspective view of the multiple rack apparatus and its position with respect to the storage outlet and to the automatic system.
Figure 2:
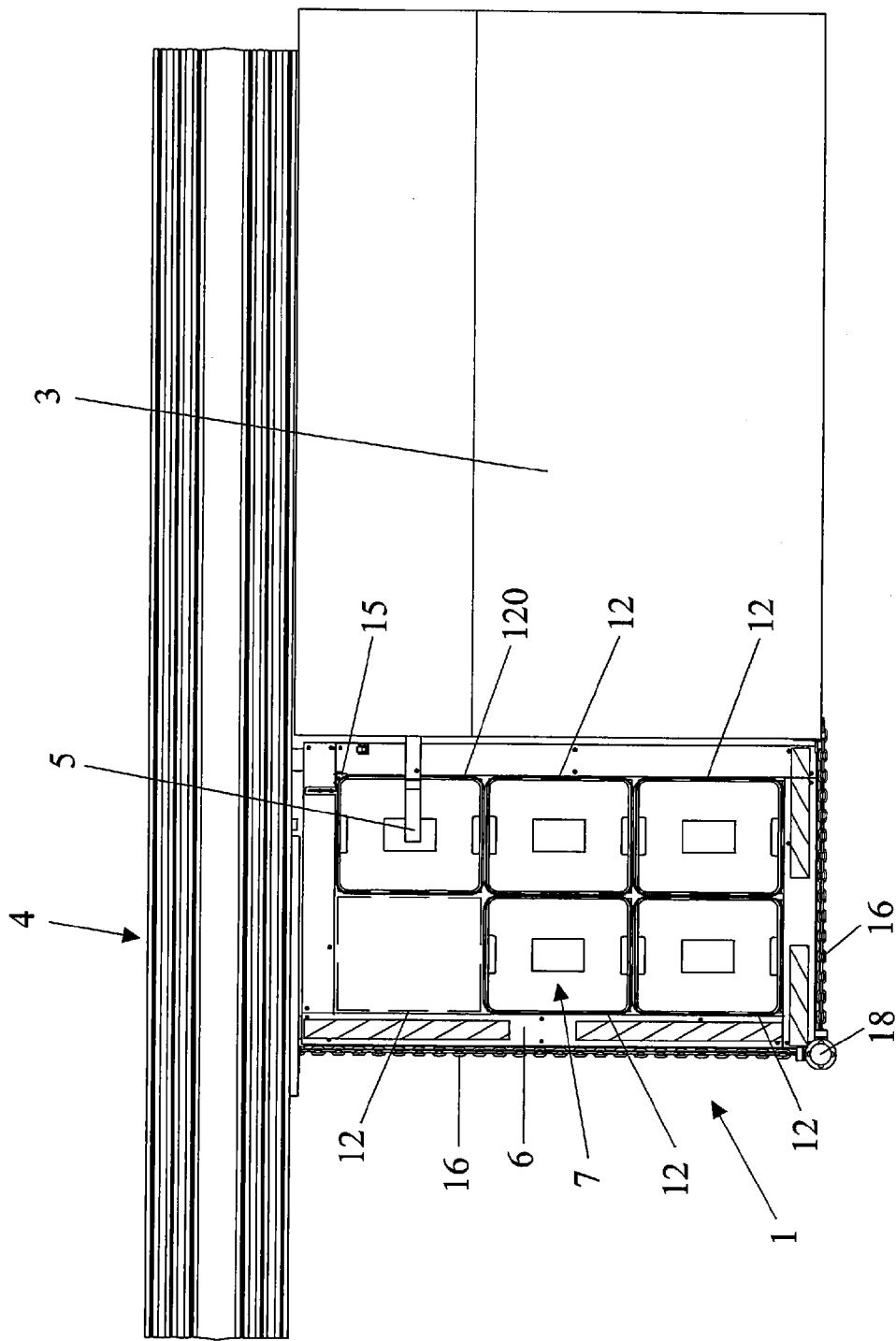
FIG. 2 is a top plan view of the illustration shown in FIG. 1.

An apparatus 1 for accommodating containers of biological products, or test tubes, 2 unloaded from a storage 3 is located by the side of the storage 3, which in turn is used for loading/unloading test tubes 2 to/from an automation system 4, only one portion of which is shown (FIGS. 1, 2).

In particular, apparatus 1 is adjacent to storage 3 which has an outlet tube 5 used for eliminating the test tubes 2 from storage 3. Indeed, the test tubes 2 remain in storage 3 for a given period of time in order to be recalled if needed along system 4 to carry out new tests or to repeat a previous test; once the maximum permanence time of the test tubes 2 in storage 3 has elapsed, after which they must be eliminated because the biological material contained inside is considered no longer intact, and therefore no longer usable for diagnostic purposes, the test tubes 2 are picked by a handling device inside storage 3 and routed to the outlet tube 5.

Storage 3 is thus advantageously a known refrigerated storage, however the flowing description does not change in case of a general apparatus for preserving test tubes 2 of biological material having an outlet tube 5.

Figure 4:
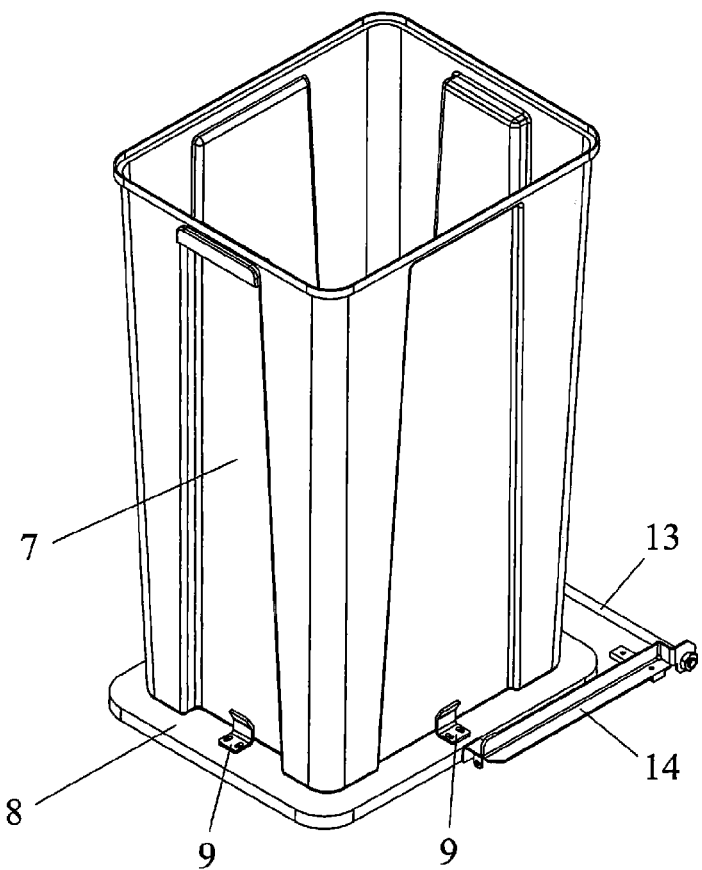
FIG. 4 shows a perspective view of the rack and the platform on which it rests.
Figure 5:
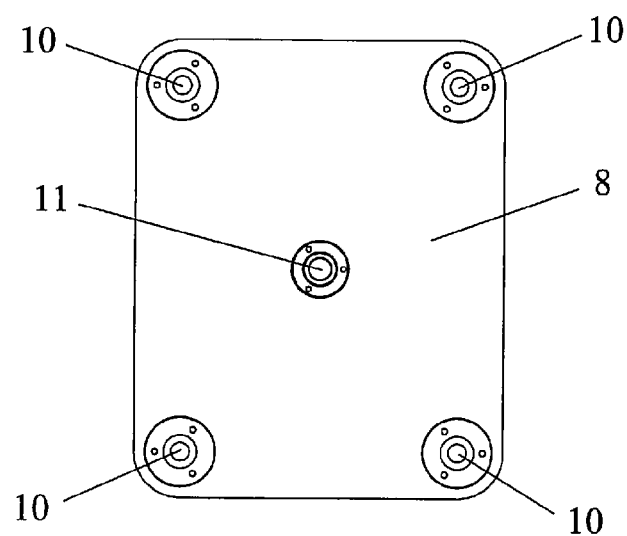
FIG. 5 shows a bottom view of the platform.

Apparatus 1 comprises a platform 6 which houses a given number of racks 7 therein, each of which rests on a platform 8 having dimensions substantially equal to the base of each rack 7. Each platform 8 has four retainers 9 on the upper surface, one on each side, in order to fix rack 7 (FIG. 4), and four wheels 10 on the lower surface at the four corners thereof to favor their sliding movement along the surface of platform 6, and a rubber pad 11 in the middle (FIG. 5).

On platform 6 there is an odd number of racks 7, and thus of platforms 8, which move either horizontally or vertically and occupy a number of dummy locations 12, 120 (shown for this reason with a dashed line in FIGS. 2 and 3) equal to the number of racks 7 plus one. In practice, one of the locations 12, 120 inside platform 6 remains empty, i.e. is not occupied by any rack 7, according to different instants.

Figure 3:
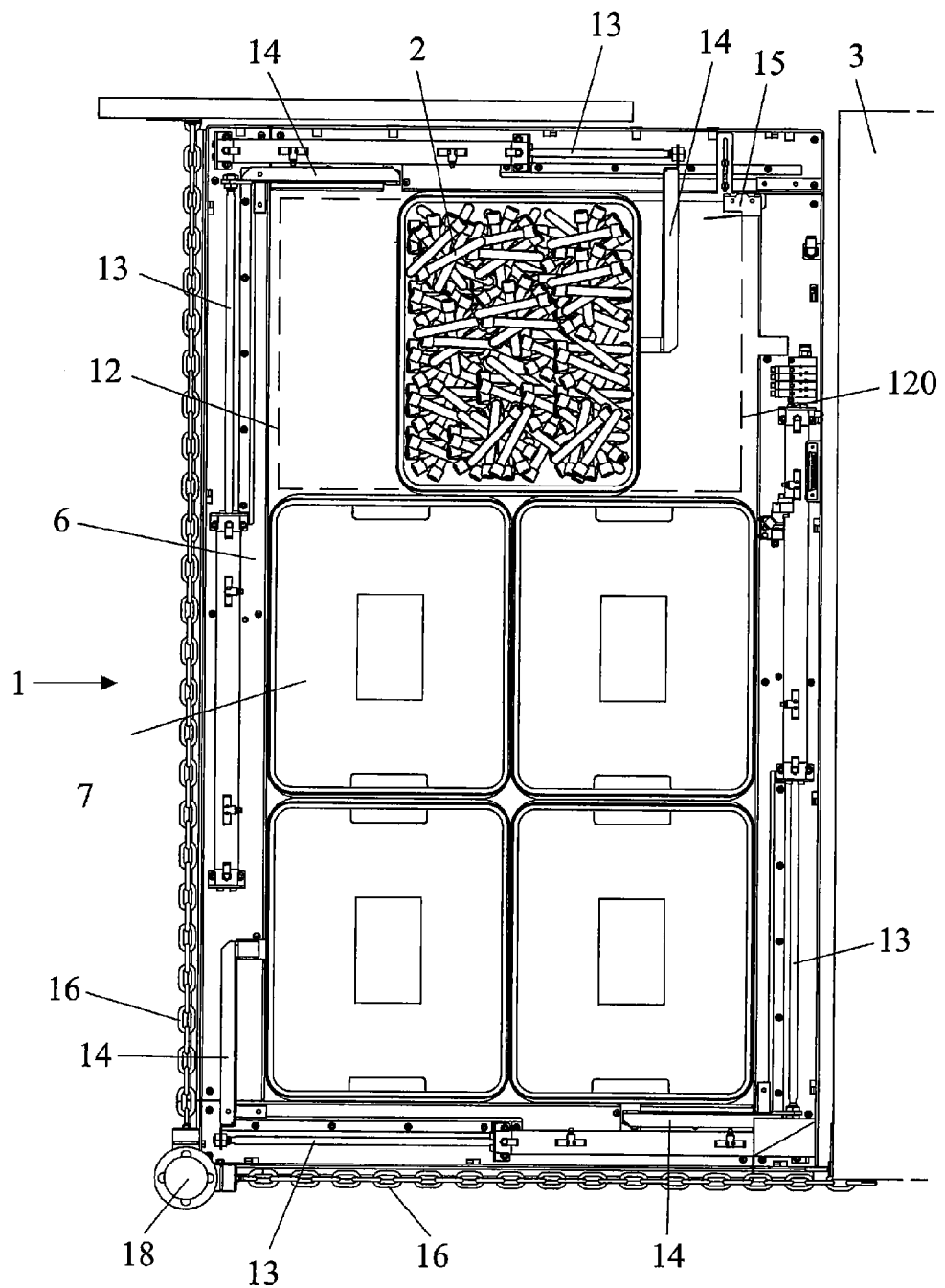
FIG. 3 is a top plan view of a detail of the apparatus during a step of sliding a rack, the outlet tube being removed and some details arranged along the perimeter of the platform being highlighted.

In the embodiment shown, there are five racks 7, and thus six locations 12, 120 but it is understood that the solution may be adapted to any number of locations 12, 120, and thus racks 7, providing that there is an even number of locations and thus an odd number of racks. Indeed, all racks 7 must be always along the perimeter of platform 6, because their sliding movement is favored by the presence of four pneumatic cylinders 13 which move precisely along the perimeter of platform 6, concealed from sight by the side profile of the platform 6 itself (they are shown in FIG. 3 only because such a side profile has been removed); a lever 14 is respectively coupled thereto, perpendicularly to cylinder 13, which lever 14 slides with cylinder 13 and impacts against the side surface of platform 8 (FIG. 4), thus moving the respective rack 7 from one location 12, 120 to the next.

There is also provided a sensor 15 for detecting the presence of one of racks 7 in the operating location 120, i.e. the location which is vertical to the outlet tube 5 which accommodates the test tubes 2 unloaded from storage 3.

Apparatus 1 is completed by two chains 16 which delimit the area in which apparatus 1 is present for safety purposes; furthermore, a light signaler 18 which acts as a warning/danger signal when handling racks 7 is fitted on the top of the upright 17 to which the two chains 16 are fixed.

A control unit 30 of storage 3 keeps count of the test tubes 2 unloaded through tube 5 into the rack 7 which occupies the operating location 120. In turn, the control unit 30 interfaces with a control unit 40 of the whole automation system 4, which keeps count instead of the number of full racks 7 inside apparatus 1.

The starting of the procedure of unloading the test tubes 2 which are no longer usable for diagnostic purposes from storage 3 presumes the presence of a rack 7 in operating location 120, corresponding to the vertical with respect to the outlet tube 5 (and shown on the top right in FIGS. 2 and 3).

If there is no rack 7 in such an operating location 120, the test tube outlet 2 from storage 3 remains blocked until apparatus 1 positions a rack 7 in such a location 120; the unloading of the test tubes 2 from storage 3 is started when such a situation, appropriately detected by the rack 7 engaging the presence sensor 15, is achieved.

According to an estimate on the capacity of each rack 7 made beforehand, storage 3 is configured to count (by means of its control unit 30) the number of test tubes 2 sequentially unloaded and to activate the rotation of the racks 7 in apparatus 1 if a rack 7 is filled, i.e. when the count has reached the predetermined number which denotes the full rack 7 situation; at the same time, the control unit 30 of storage 3 warns the control unit 40 of the whole system 4, and the latter increases the count of the number of full racks 7 within apparatus 1 by one unit.

The control unit 30 of storage 3, in full rack 7 condition, blocks the unloading of the test tubes 2 from tube 5, while activating the sliding procedure of racks 7, which includes the actuation, in sequence, of each of the cylinders 13 and of the corresponding lever 14 to move the racks 7 from one location 12, 120 to the next. FIG. 3 shows, for example, a first of such sliding movements, i.e. the separation of the newly filled rack 7 from the operating location 120.

In the embodiment shown in the figures, after such a first sliding movement, the operating location 120 may be immediately filled with a new empty rack 7; the engagement of such a new rack 7 with the presence sensor 15 allows storage 3 to resume the unloading operation of new test tubes 2 through the tube 5. In the meantime, the sliding movement of the racks 7 along the perimeter of the platform 6 of apparatus 1 is completed, i.e. the racks 7 resume the positions shown in FIG. 2.

As previously mentioned, the levers 14 actually abut against platforms 8 at the base of each rack 7 (FIG. 4); the size of the platforms 8 is calibrated to fit perfectly into the area occupied by platform 6 (minus the empty location 12, 120), and therefore their movement is ensured along only one direction. The sliding movement of platform 8 along platform 6 is certainly favored by the presence of the wheels 10 on the lower base. Each lever 14, by operating on the side surface of a platform 8, can move one or more platforms 8, and thus racks 7, according to the circumstances and according to the position of the empty location 12, 120.

Racks 7 thus move only either horizontally or vertically by exploiting the degree of freedom offered by the presence of the empty location 12, 120 each time; in essence, the effect which is obtained is thus that of an anticlockwise rotation of racks 7 about the perimeter of platform 6.

As soon as any movement of the racks 7 starts along the whole apparatus 1, the light signaler 18 starts blinking to indicate that the moving maneuver of racks 7 is about to start. Afterwards, the light signaler 18 remains fixed during such a movement and eventually goes out at the end.

The substantial rotation of the racks 7 is repeated, as described above, for each operation of filling a new rack 7; in the meantime, the count of the number of filled racks 7 is always increased by one unit by the control unit 40, and at the same time the unloading of the test tubes 2 from storage 3 is suspended until a new empty rack 7 reaches the operating location 120.

After having filled the last rack 7 (i.e. the fifth in the embodiment shown in the figures), the control unit 40, the count of which has reached the maximum allowed value, i.e. the number of such racks 7, activates a "full rack" indication.

At this point, the laboratory operators must empty the racks 7; storage 3 remains blocked for unloading the test tubes 2 and also for any other activity (i.e. storage 3 is offline) until this occurs. Obviously, no other rotation of racks 7 occurs inside apparatus 1.

One or more operators manually remove racks 7, empty them all advantageously into specific containers provided for the final disposal of the test tubes 2, and reposition them over the respective platforms 8 (naturally, each rack 7 must be exactly on the platform 8 which housed it before), and afterwards a reset is controlled on the control unit 8, which allows to reset the count and restart the operation of storage 3; the unloading of the test tubes 2 through tube 5, and therefore the filling of the racks 7, may be resumed.

As the count about the filling of a single rack 7 and the count about the number of filled racks 7 are, as mentioned above, carried out by two different entities, i.e. by the control unit 30 of storage 3 and by the control unit 40 of automation system 4, respectively, it is convenient not to empty a single full rack 7 but to wait for all racks 7 to be filled. Indeed, the manual removal of a single rack 7 from apparatus 1 for the purpose of emptying it on the fly while storage 3 is not blocked, may not be correctly discriminated by the control unit 40, which can only carry out a sequential count up to the maximum allowed number (five, in the embodiment shown) and reset the count once all the racks 7 have been emptied, but cannot decrease such a count if only one rack 7 is emptied.

Apparatus 1 is set up to be left running particularly during the night, in parallel to the operation of storage 3 (which must count the unloaded test tubes 2) and of automation system 4 (which must possibly increase the count of the filled racks 7). In all cases, if system 4 is stopped due to logistic needs of the test laboratory, storage 3 and automation system 4 (in particular, the respective control units 30 and 40) store their counts for the subsequent restart, and therefore there is no risk of losing track of the situation which was previously achieved (e.g. the day before).

The innovative aspect of the invention is thus the possibility of increasing the time which elapses between the operations of emptying the racks 7 which collect the unloaded test tubes 2 (because they can no longer be used for diagnostic purposes) from a storage 3 used for their preservation by the laboratory operators in charge. The known solutions indeed use a single rack, which presumably must be emptied with greater frequency, thus involving operators more.

In the known systems, it is thus difficult to image leaving storage 3, and consequently apparatus 1, running at night, because a single rack 7 would be certainly filled up during that time, and therefore storage 3 would sooner or later be blocked, substantially thwarting the benefit of keeping it on at night; instead, the above-described solution supports a fivefold number of unloaded test tubes 2 (in the described embodiment), and can thus run for one entire night without totally filling up all the racks 7, and thus blocking the activities of storage 3. This allows to greatly increase the operating efficiency of storage 3 and, by extension, of the whole automation system 4.

The invention thus described is susceptible to several changes and variants, all within the scope of the inventive concept.

In practice, the materials used as well as the shapes and size may be any, according to needs.

The invention claimed is:

1. A laboratory automation system comprising a storage for preservation of biological product containers and a multiple rack apparatus for accommodating biological product containers unloaded from the storage, wherein said multiple rack apparatus comprises an odd number of racks which can be housed within a base platform having a number of locations which is equal to said odd number plus one, said racks being horizontally or vertically slidable from one location to another of said base platform, taking advantage of the presence of a temporarily empty location, said racks, furthermore, in turn occupying an operating location which, being vertical with respect to an outlet tube of said storage, accommodates said biological product containers unloaded from said storage;
   wherein said storage comprises a storage control unit which keeps count of the biological product containers unloaded through said outlet tube into one of said racks which in turn occupies the operating location,
   wherein said multiple rack apparatus comprises a presence sensor adapted to detect the presence of one of said racks in said operating location, said presence sensor being operatively connected to said storage control unit to block said outlet tube until the presence of one of said racks is not detected in said operating location and, when said rack is detected, to automatically resume an unloading operation of said biological product containers through said outlet tube, and
   wherein said storage control unit activates the sliding of said racks from one location to another, when one of said racks which in turn occupies the operating location is fulfilled with a predetermined number of biological product containers.

2. The laboratory automation system according to claim 1, wherein each of said racks rests on a single rack platform, the dimensions of which are adapted so that the totality of said single rack platforms exactly fills the surface of said base platform, except said temporarily empty location.

3. The laboratory automation system according to claim 1, wherein said single rack platform has retainers on an upper base so as to retain said racks and wheels on a lower base so as to favour the sliding thereof along said locations of said base platform.

4. The laboratory automation system according to claim 1, wherein the sliding of one or more of said racks from one location to another of said base platform is achieved by means of impact of a lever protruding from the perimeter of said base platform against the lateral surface of one of said single rack platforms housing one of said racks, each side of said base platform having said lever.

5. The laboratory automation system according to claim 4, wherein said sliding of said racks from one location to another is achieved by a plurality of pneumatic cylinders which move along the perimeter of said base platform.

6. The laboratory automation system according to claim 1, wherein said multiple rack apparatus comprises a light signaler adapted to act as a warning danger signal during the sliding of said racks.

7. The laboratory automation system according to claim 1, wherein the laboratory automation system comprises a laboratory automation system control unit which keeps count of the number of said racks fulfilled with said biological product containers.

8. The laboratory automation system according to claim 5, wherein each of said levers is coupled with each of said pneumatic cylinders, said lever sliding with said pneumatic cylinder to impact against the side surface of said single rack platform.

* * * * *